(12) United States Patent
Winslow et al.

(10) Patent No.: US 9,955,984 B2
(45) Date of Patent: May 1, 2018

(54) AUGMENTED GLENOID AND METHOD FOR PREPARATION

(71) Applicant: Biomet Manufacturing, LLC, Warsaw, IN (US)

(72) Inventors: Nathan A. Winslow, Warsaw, IN (US); Thomas M. Vanasse, South Bend, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 530 days.

(21) Appl. No.: 14/594,667

(22) Filed: Jan. 12, 2015

(65) Prior Publication Data

US 2016/0199074 A1     Jul. 14, 2016

(51) Int. Cl.
*A61B 17/16* (2006.01)
*A61B 17/17* (2006.01)

(52) U.S. Cl.
CPC ...... *A61B 17/1778* (2016.11); *A61B 17/1684* (2013.01); *A61B 17/17* (2013.01); *A61B 17/1739* (2013.01)

(58) Field of Classification Search
CPC . A61B 17/16; A61B 17/1662; A61B 17/1684; A61B 17/17; A61B 17/1739; A61B 17/1778; A61B 2017/1602
USPC .......................................................... 606/96
See application file for complete search history.

(56) References Cited

U.S. PATENT DOCUMENTS

| | | | |
|---|---|---|---|
| 5,306,278 A | 4/1994 | Dahl et al. | |
| 5,624,445 A * | 4/1997 | Burke | A61B 17/1659 409/178 |
| 5,741,266 A * | 4/1998 | Moran | A61B 17/1778 606/104 |
| 5,743,915 A | 4/1998 | Bertin et al. | |
| 5,769,856 A * | 6/1998 | Dong | A61F 2/4081 606/80 |
| 6,364,910 B1 * | 4/2002 | Shultz | A61B 17/1782 606/86 R |

(Continued)

FOREIGN PATENT DOCUMENTS

WO   WO-2014176118 A1   10/2014
WO   WO-2016115109 A1   7/2016

OTHER PUBLICATIONS

"International Application Serial No. PCT/US2016/013009, International Search Report dated Apr. 14, 2016", 7 pgs.

(Continued)

*Primary Examiner* — Eric S Gibson
(74) *Attorney, Agent, or Firm* — Schwegman Lundberg & Woessner, P.A.

(57) ABSTRACT

A system for augmenting a glenoid in preparation for implantation of a glenoid implant includes an augment guide block. The augment guide block includes a body having a guide slot angularly extending from a first surface to a second surface at an angle α, a plurality of alignment members extending from the first surface of the body that couple the body to the glenoid at locations that correspond to locations where a central peg and a peripheral peg will couple the glenoid implant to the glenoid. The system also includes an augmenting device that is configured to be received within the slot, and that is operable to augment the glenoid at the angle α, wherein the angle α corresponds to a surface of the glenoid implant.

17 Claims, 6 Drawing Sheets

(56) References Cited

U.S. PATENT DOCUMENTS

| | | | |
|---|---|---|---|
| 6,699,289 B2* | 3/2004 | Iannotti | A61B 17/1684 623/19.11 |
| 7,927,335 B2* | 4/2011 | Deffenbaugh | A61B 17/1617 606/87 |
| 8,486,076 B2* | 7/2013 | Chavarria | A61B 17/1659 606/85 |
| 8,556,980 B2* | 10/2013 | Deffenbaugh | A61F 2/30734 623/19.11 |
| 8,790,350 B2* | 7/2014 | Deffenbaugh | A61B 17/1617 606/87 |
| 9,033,990 B2* | 5/2015 | Iannotti | A61B 17/17 606/104 |
| 9,089,348 B2* | 7/2015 | Chavarria | A61B 17/1659 |
| 9,119,643 B2* | 9/2015 | Winslow | A61B 17/1739 |
| 9,149,362 B2* | 10/2015 | Deffenbaugh | A61B 17/1617 |
| 9,320,527 B2* | 4/2016 | Kehres | A61B 17/1617 |
| 9,351,743 B2* | 5/2016 | Kehres | A61B 17/1739 |
| 2004/0230197 A1* | 11/2004 | Tornier | A61B 17/1778 606/87 |
| 2006/0074430 A1* | 4/2006 | Deffenbaugh | A61B 17/1617 606/87 |
| 2007/0055380 A1* | 3/2007 | Berelsman | A61F 2/4081 623/19.11 |
| 2009/0149890 A1* | 6/2009 | Martin | A61B 17/1717 606/316 |
| 2010/0268238 A1* | 10/2010 | Sikora | A61B 17/1778 606/87 |
| 2011/0029088 A1* | 2/2011 | Rauscher | A61B 17/1778 623/19.11 |
| 2011/0035013 A1* | 2/2011 | Winslow | A61F 2/4003 623/19.13 |
| 2011/0144651 A1* | 6/2011 | Deffenbaugh | A61B 17/1617 606/87 |
| 2012/0109135 A1 | 5/2012 | Bailey | |
| 2012/0109226 A1* | 5/2012 | Iannotti | A61B 17/88 606/86 R |
| 2012/0197258 A1* | 8/2012 | Chavarria | A61B 17/1659 606/85 |
| 2012/0239042 A1* | 9/2012 | Lappin | A61B 17/1617 606/80 |
| 2012/0239043 A1* | 9/2012 | Lappin | A61B 17/1631 606/80 |
| 2012/0239051 A1* | 9/2012 | De Wilde | A61F 2/4081 606/96 |
| 2013/0096564 A1* | 4/2013 | Winslow | A61B 17/1739 606/96 |
| 2013/0110116 A1* | 5/2013 | Kehres | A61B 17/1739 606/96 |
| 2013/0267958 A1* | 10/2013 | Iannotti | A61B 17/17 606/87 |
| 2014/0066933 A1* | 3/2014 | Ek | A61F 2/30734 606/80 |
| 2014/0207141 A1* | 7/2014 | Kehres | A61B 17/1617 606/80 |
| 2014/0257304 A1* | 9/2014 | Eash | A61B 17/1778 606/87 |
| 2014/0257495 A1* | 9/2014 | Goldberg | A61F 2/4081 623/19.11 |
| 2014/0303738 A1* | 10/2014 | Deffenbaugh | A61B 17/1617 623/19.11 |
| 2014/0343556 A1* | 11/2014 | Valenti | A61B 17/1778 606/87 |
| 2015/0157462 A1* | 6/2015 | Ek | A61F 2/4081 623/19.11 |
| 2015/0320430 A1* | 11/2015 | Kehres | A61B 17/1617 606/87 |
| 2016/0089164 A1* | 3/2016 | Winslow | A61B 17/1739 606/80 |
| 2016/0143749 A1* | 5/2016 | Holovacs | A61F 2/4081 623/19.11 |
| 2016/0199074 A1* | 7/2016 | Winslow | A61B 17/1739 606/80 |
| 2016/0310285 A1* | 10/2016 | Kovacs | A61B 17/15 |
| 2016/0374697 A1* | 12/2016 | Kehres | A61B 17/1739 606/87 |

OTHER PUBLICATIONS

"International Application Serial No. PCT/US2016/013009, Written Opinion dated Apr. 14, 2016", 6 pgs.

Neer, Charles S., et al., "Glenoid Bone-Grafting in Total Shoulder Arthroplasty", The Journal of Bone and Joint Surgery, vol. 70-A, No. 8 (Sep. 1998), pp. 1154-1162.

Comprehensive® Total Shoulder System Featuring Comprehensive® Access Glenoid Instrumentation Surgical Technique. Biomet® Orthopedics. (2012) pp. 1-56.

Exactech Shoulder Operative Technique; Equinoxe Platform Sholder System Jan. 2013 Exactech 718-01-30 Rev. D, Equinoxe Primary/Reverse Op Tech 0413, 60 pp.

Global® Steptech® Anchor Peg Glenoid Surgical Technique. DePuy Synthes Joint Reconstruction. (2014) pp. 1-32.

"International Application Serial No. PCT/US2016/013009, International Preliminary Report on Patentability dated Jul. 27, 2017", 8 pgs.

* cited by examiner

AUGMENTED GLENOID AND METHOD FOR PREPARATION

FIELD

The present disclosure relates to system and method for augmenting a glenoid in preparation for a shoulder arthroplasty procedure where a shoulder implant including an augment is to be fixed to the glenoid.

BACKGROUND

This section provides background information related to the present disclosure which is not necessarily prior art.

In cases of severe glenoid wear, it can be difficult to return the shoulder joint to a near neutral version using a standard glenoid implant. In these instances, the surgeon performing shoulder arthroplasty needs to compromise by inserting the glenoid implant at a non-ideal angle, or by removing a significant amount of native bone from the shoulder joint. Recently, glenoid implants with augments have been developed to account for glenoids having severe wear or defects.

SUMMARY

This section provides a general summary of the disclosure, and is not a comprehensive disclosure of its full scope or all of its features.

According to a first aspect of the present disclosure, a guide device is provided for augmenting an anatomic structure. The guide device includes a body including an upper surface, a lower surface, and a peripheral surface that connects each of the upper and lower surfaces. A guide slot extends between the upper surface and the lower surface of the body at an angle $\alpha$ that is non-parallel and non-perpendicular relative to the upper and lower surfaces, and the guide slot is configured for receipt of a shaping device that shapes the anatomic structure at the angle $\alpha$. A plurality of alignment members extends from the lower surface that removably couple the body to the anatomic structure.

According to the first aspect, the alignment members include a central alignment member and a peripheral alignment member.

According to the first aspect, the angle $\alpha$ is in the range of 10 degrees to 75 degrees.

According to the first aspect, the body is trapezoidal-shaped.

According to the first aspect, the guide device further includes a handle for orienting the body relative to the anatomic structure.

According to the first aspect, the body includes a boss for attachment with the handle.

According to the first aspect, the shaping device is a burr.

According to the first aspect, the anatomic structure is a glenoid.

According to the first aspect, the guide slot is linear.

According to the first aspect, the guide slot includes an inlet and an outlet, and includes radius of curvature between the inlet and the outlet.

According to a second aspect of the present disclosure, a method for performing shoulder arthroplasty is provided. The method includes preparing the glenoid for receipt of a glenoid implant; and attaching an augment guide block to the glenoid. The augment guide block includes a guide slot extending between a upper surface and a lower surface of the augment guide block at an angle $\alpha$ that is non-parallel and non-perpendicular relative to the upper and lower surfaces, and that is configured for receipt of a shaping device that shapes the glenoid at the angle $\alpha$. The method also includes augmenting the glenoid with the shaping device at the angle $\alpha$; and attaching the glenoid implant to the glenoid after augmenting the glenoid.

According to the second aspect, the angle $\alpha$ is in the range of 10 degrees to 75 degrees.

According to the second aspect, the method further comprises orienting the augment guide block relative to the glenoid using a handle.

According to the second aspect, the method further comprises selecting the augment guide block from a plurality of augment guide blocks that each include a guide slot having a different angle $\alpha$.

According to the second aspect, the guide slots are linear or curved.

According to the second aspect, the method further comprises determining pre-operatively a portion of the glenoid that requires shaping.

According to the second aspect, the method further comprises selecting the augment guide block from a plurality of augment guide blocks that each include a guide slot having a different angle $\alpha$ based on the portion of the glenoid that requires the shaping.

According to a third aspect of the present disclosure, a system for augmenting a glenoid in preparation for implantation of a glenoid implant including a central peg and a peripheral peg is provided. The system includes an augment guide block. The augment guide block includes a body having a guide slot angularly extending from a first surface to a second opposing surface at an angle $\alpha$, a plurality of alignment members extending from the first surface of the body that removably couple the body to the glenoid at locations that correspond to locations where the central peg and peripheral peg will couple the glenoid implant to the glenoid, and a boss formed on the second surface. A handle is configured to mate with the boss, and is operable to orient the augment guide block relative to the glenoid. The system also includes an augmenting device that is configured to be received within the slot, and that is operable to augment the glenoid at the angle $\alpha$, wherein the angle $\alpha$ corresponds to a surface of the glenoid implant.

According to the third aspect, the alignment members include a central alignment member and a peripheral alignment member.

According to the third aspect, the angle $\alpha$ is in the range of 10 degrees to 75 degrees.

According to the third aspect, the body is trapezoidal-shaped.

According to the third aspect, the augmenting device is a burr.

According to the third aspect, the guide slot is linear.

According to the third aspect, the guide slot includes an inlet and an outlet, and includes radius of curvature between the inlet and the outlet.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
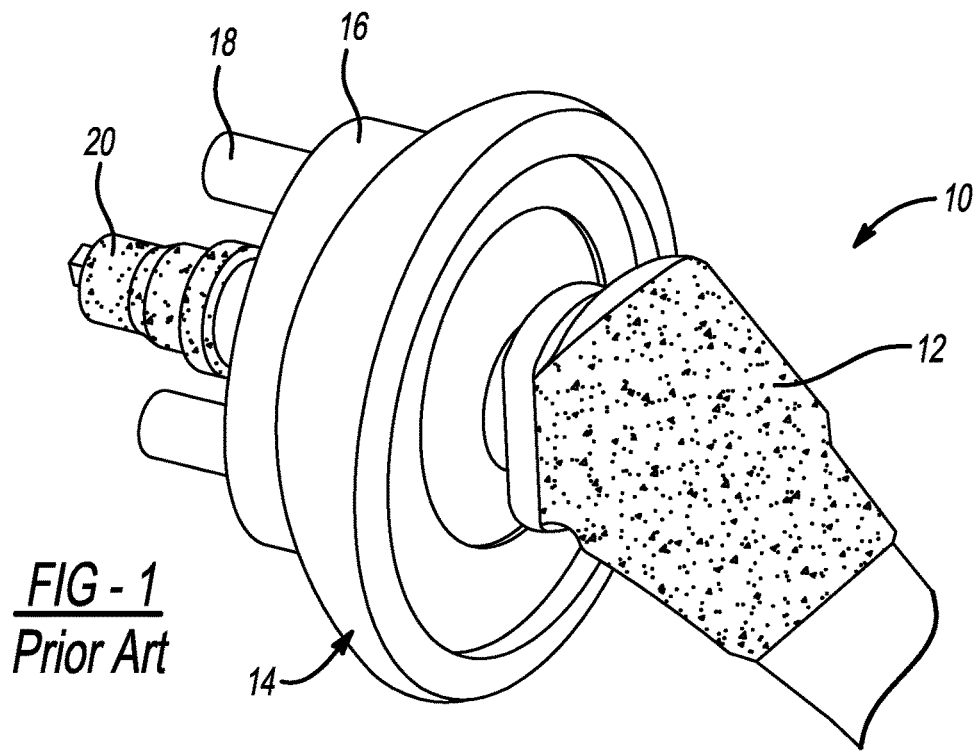
FIG. 1 is a perspective view of a prior art implant for anatomic shoulder arthroplasty.
Figure 2A:
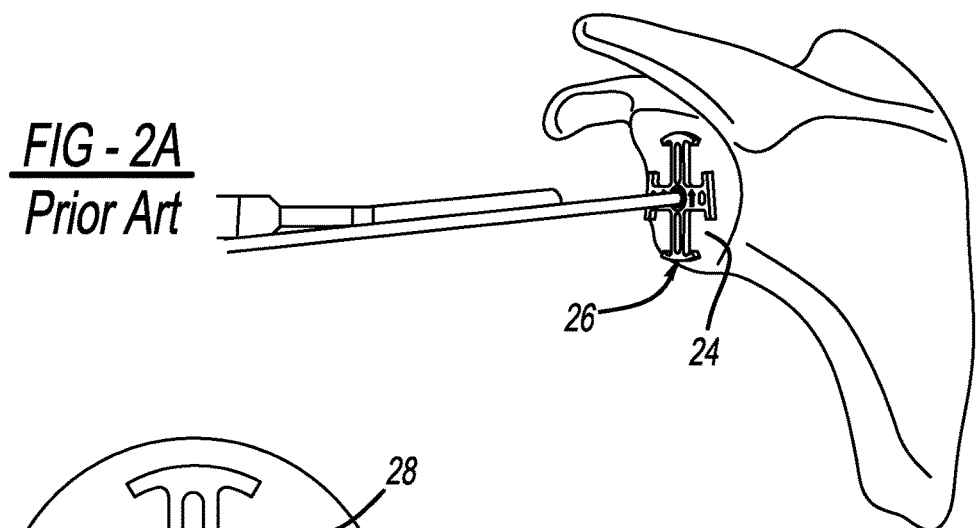
FIGS. 2A and 2B illustrate a prior art guide pin sizer device used to insert a guiding pin into a glenoid.
Figure 2B:
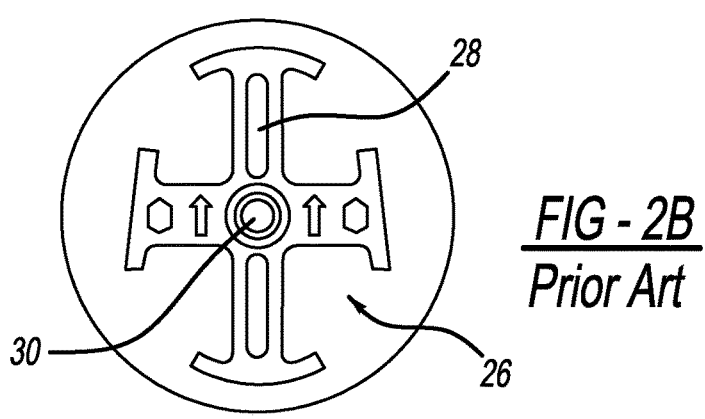
Figure 3:
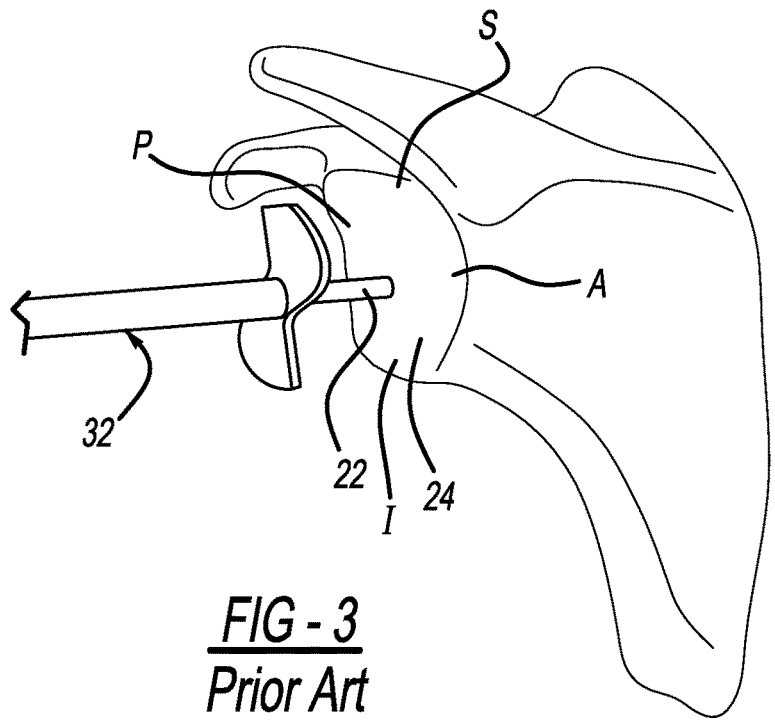
FIG. 3 illustrates a prior art reamer used to ream the glenoid.

FIG. 1 illustrates a prior art anatomic shoulder implant 10. The anatomic shoulder implant 10 includes a humeral stem 12, a humeral head 14 and a glenoid implant or bearing 16 with peripheral pegs 18 and a removable or non-removable central peg 20. To attach glenoid implant 16, a guiding pin 22 (FIG. 3) must first be inserted into glenoid face 24. Based on the operative shoulder, a sizer pin guide 26 is placed in the center of glenoid face 24 at the correct orientation (FIG. 2A). Slots 28 in sizer pin guide 26 are provided for visualization of glenoid face 24 (FIG. 2B). The guiding pin 22 may be inserted through center aperture 30 of pin guide 26 and carefully drilled into glenoid face 24 until the pin 22 has engaged the medial cortex of the glenoid vault. Once the pin 22 is securely placed, the sizer pin guide 26 is slidably removed from over pin 22.

Figure 4:
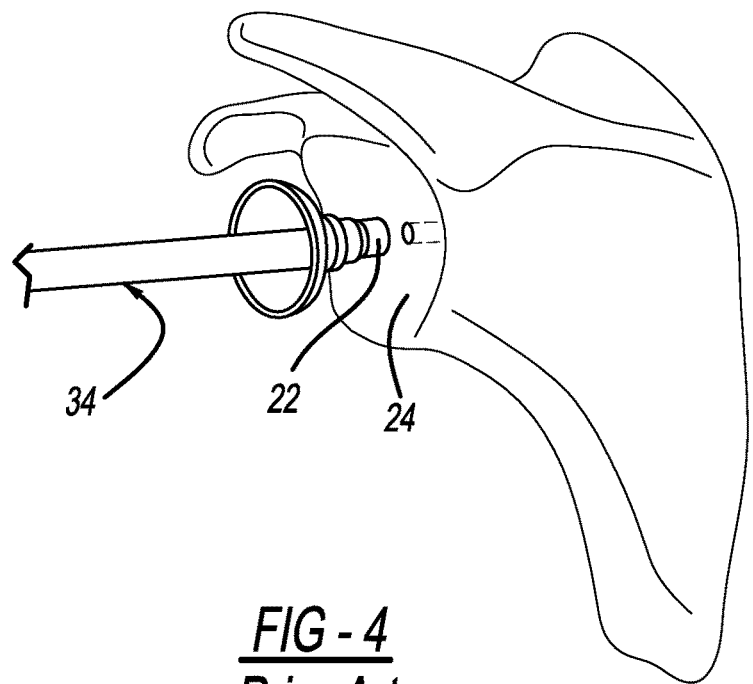
FIG. 4 illustrates a prior art central peg cutter used to prepare the glenoid for insertion of a glenoid implant including a central peg.

Next, the glenoid face 24 is prepared. A reamer 32 (FIG. 3) is selected based on the sizer pin guide 26 selected to insert guiding pin 22. The reamer 32 is inserted into the joint over the pin 22. Then, the glenoid face 24 is reamed to accommodate the glenoid implant 16. Once the desired amount of reaming is completed, a central peg cutter 34 (FIG. 4) is used to prepare the newly reamed glenoid face 24 for a geometry and size of the central peg 20. In this regard, the central peg cutter 34 is placed over pin 22 and glenoid face 24 is further reamed to prepare a central bore 35 into the glenoid face 24 for the central peg 20. After forming the central bore 35 in the glenoid face 24 for the central peg 20, the central peg cutter 34 is removed from over pin 22.

Figure 5:
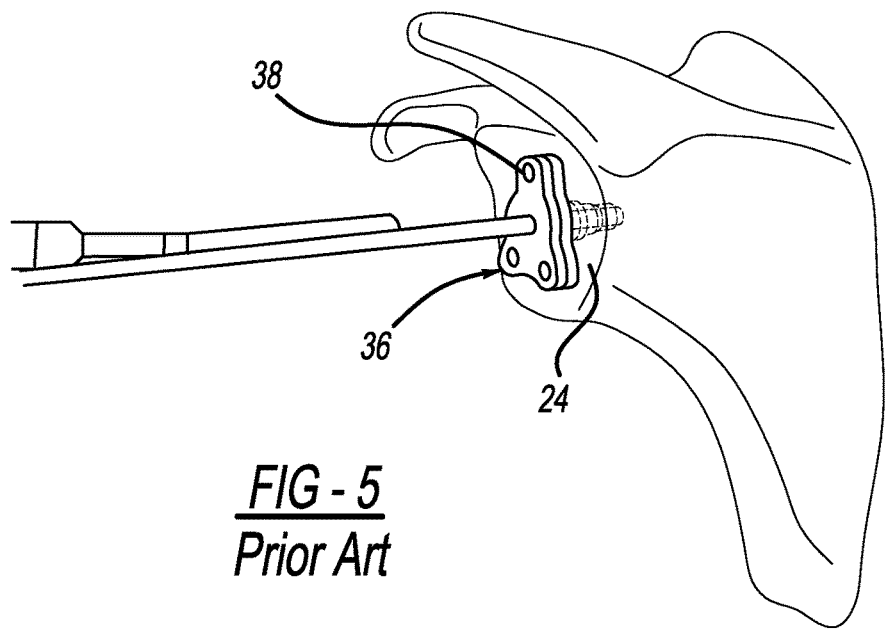
FIG. 5 illustrates a prior art peripheral peg drill guide used to determine the locations for implantation of peripheral pegs of the glenoid implant.
Figure 6:
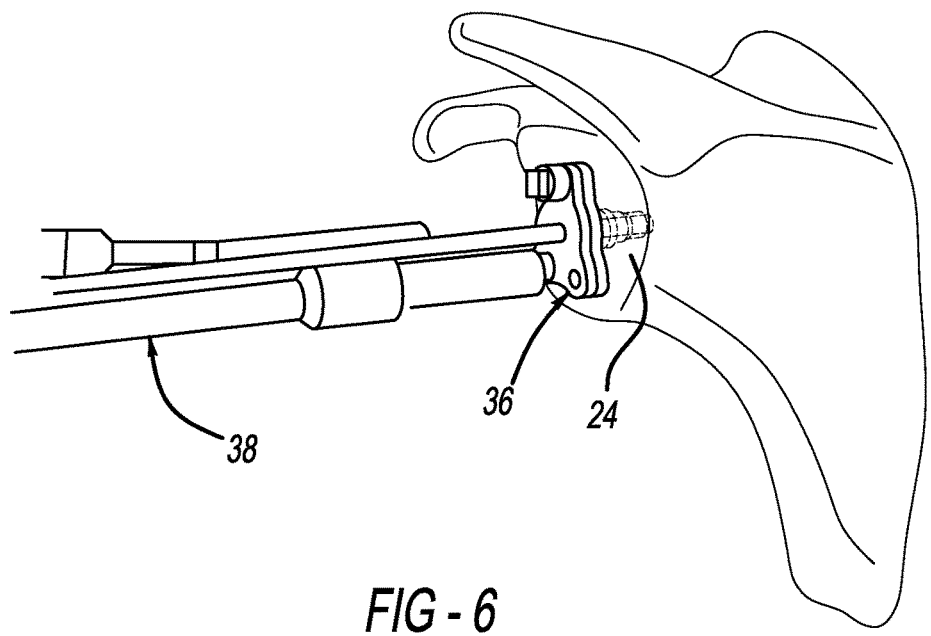
FIG. 6 illustrates a prior art drill used to drill bores in the glenoid for receipt of the peripheral pegs.
Figure 7:
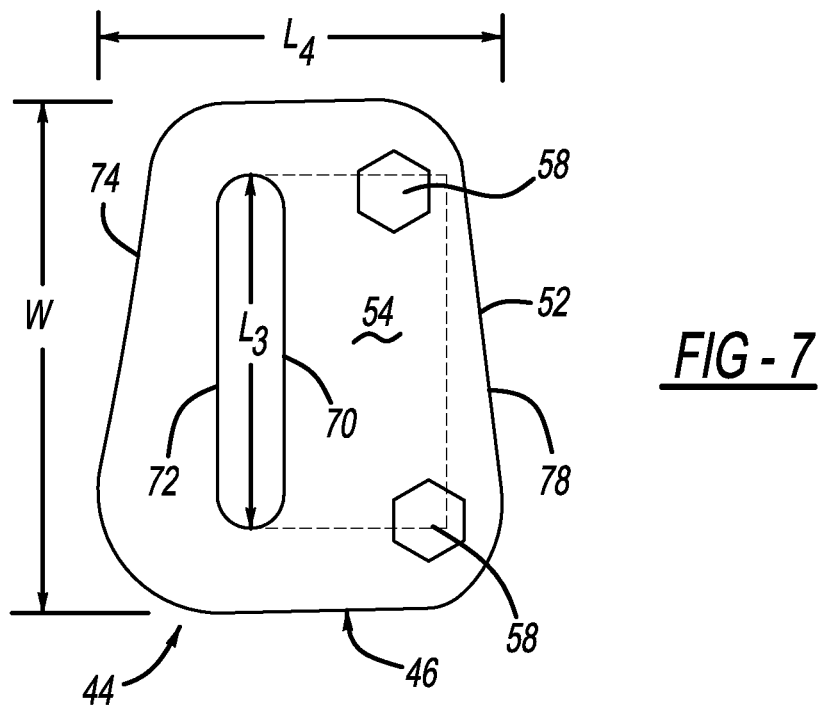
FIG. 7 is a top-perspective view of an augment guide block according to a principle of the present disclosure.
Figure 8:
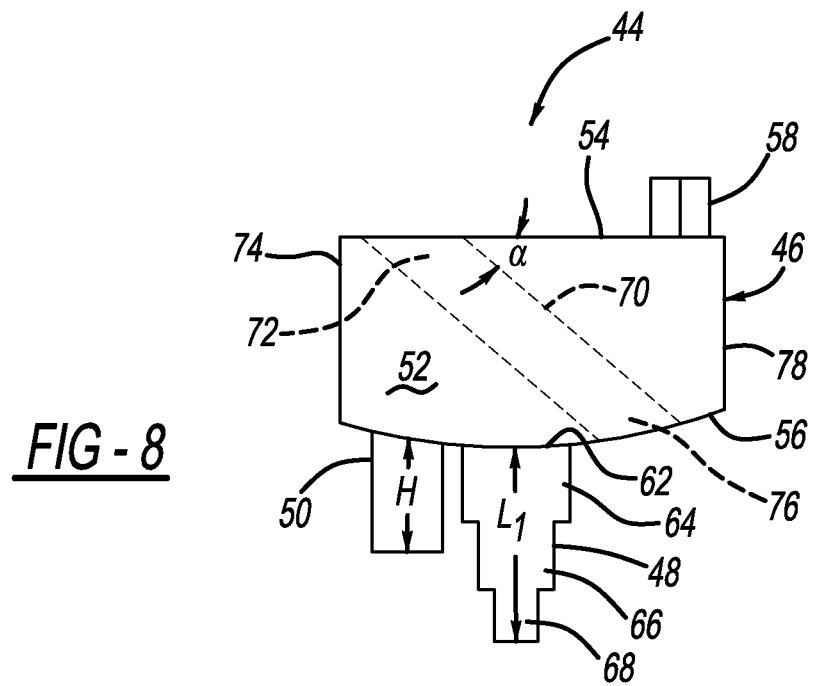
FIG. 8 is a side-perspective view of the augment guide block illustrated in FIG. 7.
Figure 9:
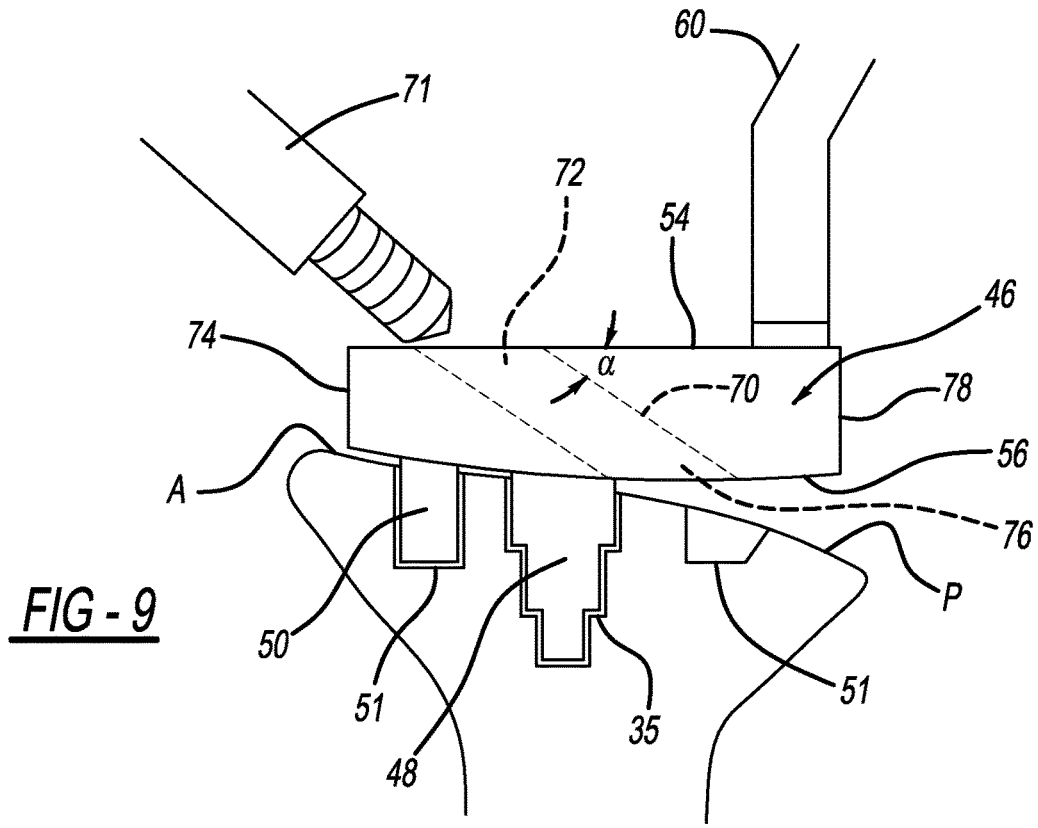
FIG. 9 is a perspective view of the augment guide block coupled to the glenoid before augmenting the glenoid.
Figure 10:
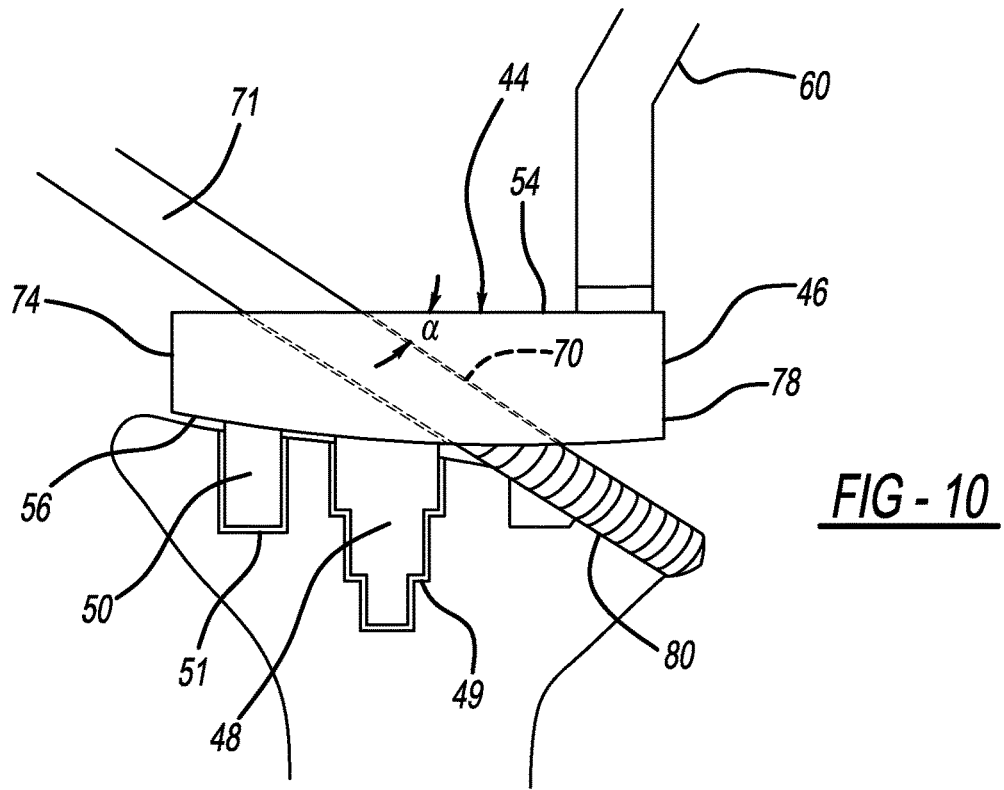
FIG. 10 illustrates augmenting of the glenoid using the augment guide block as a guide for an augmentation device.

Then, an appropriate cannulated peripheral peg drill guide 36 is selected and inserted over pin 22 and into the joint until it is fully seated against the glenoid face 24 (FIG. 5). Peripheral peg drill guide 36 includes apertures 38 that correspond to peripheral pegs 18 of the glenoid implant 16. With the drill guide 36 correctly in place, drilling is conducted with a drill 38 at each of the desired peripheral peg locations to prepare the glenoid face 24 for receipt of the peripheral pegs 18. After the peripheral peg locations are prepared, peripheral peg drill guide 36 is removed from over guiding pin 22. Each of the above-noted steps of preparing the glenoid face 24 and tools associated therewith may be found in the COMPREHENSIVE® Total Shoulder Replacement System manufactured by BIOMET® of Warsaw, Ind.

Figure 11:
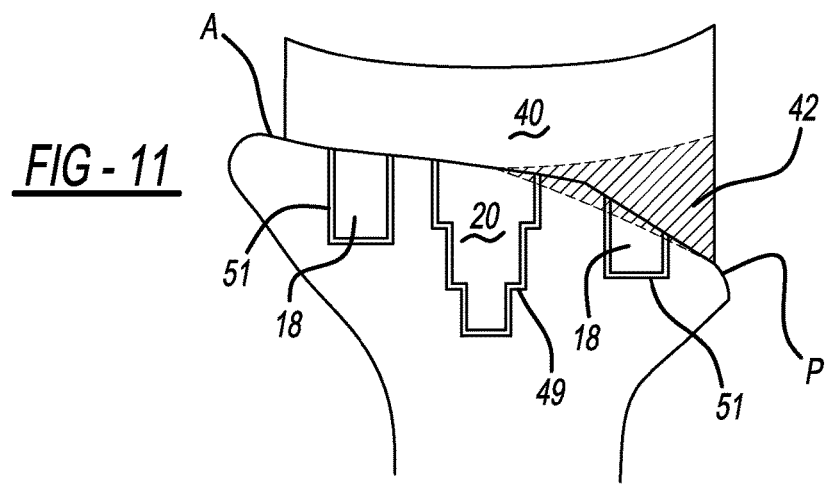
FIG. 11 is a perspective view of an exemplary augmented glenoid implant coupled to the augmented glenoid.

In cases of severe glenoid wear, it can be difficult to return the joint to near neutral version using a standard glenoid implant like bearing 16. In these instances, the surgeon has to compromise by inserting the implant 16 at a non-ideal version angle, or by removing a significant amount of native bone to gain complete backside coverage of the glenoid 24. To account for severe glenoid wear, glenoid implants 40 including an integral or modular augment 42 have been developed. For example, various augmented glenoid implants are described in U.S. patent application Ser. No. 14/459,935 filed Aug. 11, 2014, which is hereby incorporated by reference in its entirety. The glenoid face 24 must be shaped to correspond to the augment 42 of the augmented implant 40 (FIG. 11).

To shape the glenoid face 24 to correspond to the augment 42 of an augmented implant 40, the present disclosure provides an augment guide block 44 as illustrated in FIGS. 7-10. Augment guide block 44 includes a body portion 46 having a central alignment member or stem 48, and a peripheral alignment member or peg 50. While augment guide block 44 is generally shown and described herein as being monolithic or otherwise integrally formed, it should be understood that body portion 46, stem 48, and alignment peg 50 may be formed as separate components and thereafter mechanically coupled together.

Augment guide block 44 can be formed from any biocompatible material including ceramic, metals such as stainless steel or titanium, or combinations thereof. Augment guide block 44 can be formed using any suitable manufacturing process including machining, directly compression molding, and/or additive manufacturing that enables forming multiple guide blocks 44 in a single build and decreases manufacturing time. Once formed, the guide block 44 can be further processed (e.g., polished, blasted, machined, etc.) as desired. Guide block 44 may be a single-use device that is patient-specific, or may be sterilized and re-used, if desired.

Body portion 46 may include a peripheral surface 52, an upper surface 54, and a lower or bone-engaging surface 56 opposite from upper surface 54. As illustrated, in one exemplary configuration, the peripheral surface 52 may define a trapezoidal-shaped body 46. It should be understood, however, that body 46 may be parallel-piped shaped, cylindrical, oval, or any other shape desired by one skilled in the art. Upper surface 54 is generally planar and includes a pair of bosses 58. Bosses 58 allow for attachment of a handle 60, as will be described in more detail below. It should be understood, however, that bosses 58 may be replaced by recesses (not shown) without departing from the scope of the present disclosure. Lower or bone-engaging surface 56 may also be generally planar, with stem 48 and alignment peg 50 extending outward therefrom. Alternatively, as illustrated, lower surface 56 may include a slight curvature that assists in nesting guide block 44 with glenoid 24. Preferably, stem 48 extends from a center 62 of lower surface 56 and alignment peg 50 extends from a location positioned radially outward from stem 48. In addition, stem 48 is configured to mate with central bore 35 formed in glenoid face 24 by central peg cutter 34 and alignment peg 50 is configured to mate with a recess 51 formed using peripheral peg drill guide 36, as described above. In this manner, augment guide block 44 cannot rotate during augmentation of glenoid face 24.

The stem 48 may include a cylindrical proximal portion 64 unitary or connected to body portion 46, a cylindrical middle portion 66 unitary or connected to proximal portion 64, and a cylindrical distal portion 68 unitary or connected to middle portion 66. As illustrated, proximal portion 64 may include a diameter that is greater than middle portion 66, and middle portion 66 may include a diameter that is greater than distal portion 68. In this manner, stem 48 is shaped similarly to central peg 20 of anatomic implant 10. The present disclosure, however, should not be limited to such a configuration. In this regard, stem 48 may include a constant diameter along an entire length L1 thereof without departing from the scope of the present disclosure.

The alignment peg 50 may be cylindrically shaped, and have a constant diameter along an entire length L2 thereof similar to peripheral pegs 18 of implant 10. It will be appreciated, however, that alignment peg 50 may be shaped similarly to stem 48. Further, although alignment peg 50 is illustrated as having a length L2 that is less than that of stem 48, it will also be appreciated that alignment peg 50 may have a length L2 equal to that of stem 48. Alignment peg 50 and stem 48 are illustrated as being solid members, but may be hollow without departing from the scope of the present disclosure.

Augment guide block 44 includes an angled slot 70 that extends between upper surface 54 and lower surface 56 at an angle α relative to upper surface 54. The angle α is neither parallel nor perpendicular relative to each of the upper 54 and lower surfaces 56 of the body 46. Preferably, the angle α lies in the range of 10 degrees to 75 degrees relative to the upper surface 54, and is selected according to the desired amount that glenoid face 24 needs to be augmented. In this regard, the surgeon performing the shoulder arthroplasty may select the desired angle α by selecting a specific augment guide block 44 from a plurality of augment guide blocks 44 in a kit (not shown) each having slots 70 arranged at different angles α. The glenoid face 24, therefore, can be patient-specifically shaped or augmented at the appropriate angle α that is patient-specifically determined pre-operatively. Slot 70 has a length L3 that may be 50% to 80% of a width W of body 46, and may be sized for receipt of an augmenting device or burr 71 that is operable to shape or augment glenoid face 24. Further, an inlet 72 of slot 70 at upper surface 54 may be positioned proximate a first edge 74 of body 46, and an outlet 76 at lower surface 56 may be positioned proximate a second opposing edge 78 of body 46 such that slot 70 traverses body 46 at angle α from first edge 74 in length L4 direction toward second edge 78.

In the illustrated embodiment, angled slot 70 allows for preparation of a posterior surface P of the glenoid. It will be appreciated, however, that angled slot 70 can be used for preparation of an anterior surface A, a superior surface S, or an inferior surface I of glenoid face 24 (see, e.g., FIG. 3) without departing from the scope of the present disclosure. In this manner, augment guide block 44 can be used to prepare the glenoid 24 face for any defect location by rotating guide block 44 to the appropriate defect location. Alternatively, the appropriate augment guide block 44 for anterior surface A, superior surface S, or inferior surface I can be selected from the plurality of augment guide blocks in the kit (not shown) referenced above.

Figure 12:
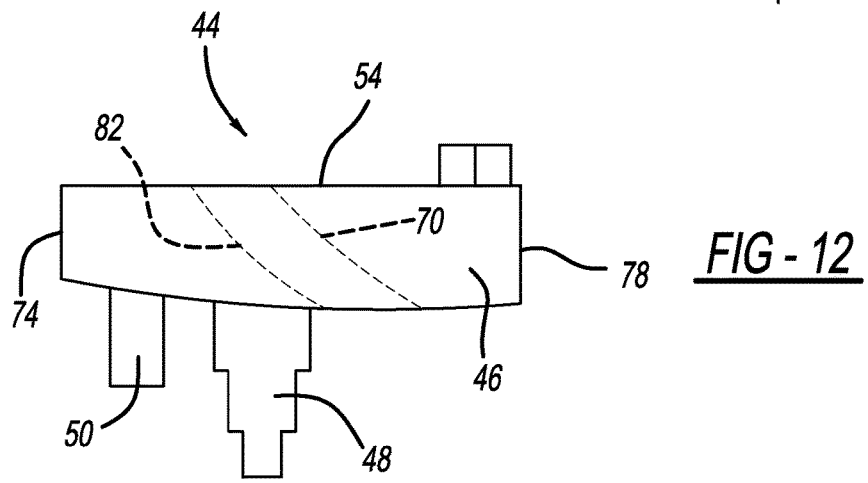
FIG. 12 is a side-perspective view of another augment guide block according to a principle of the present disclosure.
Figure 13:
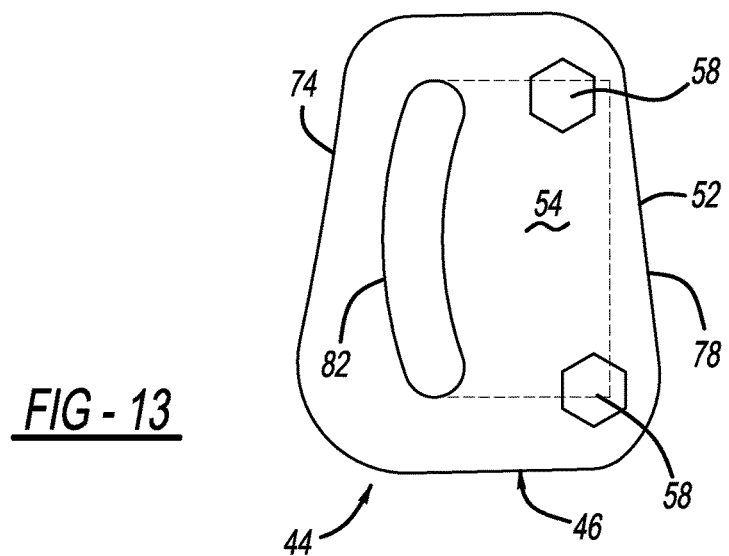
FIG. 13 is a top-perspective view of the augment guide block illustrated in FIG. 12.

Although slot 70 is illustrated as being linear to prepare glenoid 24 to include a planar surface 80 for mating with the augmented glenoid implant 40, it should be understood that slot 70 may include a radius of curvature 82 (FIG. 12) to allow glenoid 24 to prepared to mate with a correspondingly curved augmented glenoid implant (not shown). In this regard, the burr 71 used to prepare the glenoid 24 may be flexible, which allows the burr 71 to pass through curved slot 82.

Once the correct augment guide block 44 is selected based on the patient's anatomy, the augment guide block 44 is positioned on the glenoid face 24 using the handle 60, and the burr 71 is inserted into inlet 72 of slot 70 in the augment guide block 44. Under power, the burr 71 is used to remove bone at the defect location on the glenoid face 24 and, as illustrated, form planar surface 80. Also, as illustrated, the burr 71 is used to remove bone from the posterior aspect P of the glenoid 24. Once the burring is complete, the burr 71 is removed from the angled slot 70, and the augment guide block 44 is removed from the glenoid 24. A trial may then be conducted to determine fit and full seating of the augmented glenoid implant 40 on the thus-prepared glenoid face 24. If the augmented glenoid implant 40 properly mates with the augmented glenoid surface 80, the augmented glenoid implant 40 may then be implanted and fixed to the augmented glenoid surface 80 using cement or some other fixative devices such as a fastener (e.g., a bone screw, not shown).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A guide device for augmenting an anatomic structure, comprising:
    a body including an upper surface, a lower surface, and a peripheral surface that connects each of the upper and lower surfaces;
    a guide slot extending between the upper surface and the lower surface of the body at an angle α that is non-parallel and non-perpendicular relative to the upper and lower surfaces, the guide slot configured for receipt of a shaping device that shapes the anatomic structure at the angle α; and
    a plurality of alignment members extending from the lower surface that are configured to removably couple the body to the anatomic structure, the alignment members extending from the lower surface at an angle that is different from angle α when viewed in a common plane.

2. The guide device according to claim 1, wherein the alignment members include a central alignment member and a peripheral alignment member.

3. The guide device according to claim 1, wherein the angle α is in the range of 10 degrees to 75 degrees.

4. The guide device according to claim 1, wherein the body is trapezoidal-shaped.

5. The guide device according to claim 1, further comprising a handle for orienting the body relative to the anatomic structure.

6. The guide device according to claim 5, wherein the body includes a boss for attachment with the handle.

7. The guide device according to claim 1, wherein the shaping device is a burr.

8. The guide device according to claim 1, wherein the anatomic structure is a glenoid.

9. The guide device according to claim 1, wherein the guide slot is linear.

10. The guide device according to claim 1, wherein the guide slot includes an inlet and an outlet, and includes a radius of curvature between the inlet and the outlet.

11. A system for augmenting a glenoid in preparation for implantation of a glenoid implant including a central peg and a peripheral peg, comprising:

an augment guide block, the augment guide block including a body having a guide slot angularly extending from a first surface to a second opposing surface at an angle $\alpha$, a plurality of alignment members extending from the first surface of the body that are configured to removably couple the body to the glenoid at locations that correspond to locations where the central peg and peripheral peg will couple the glenoid implant to the glenoid, and a boss formed on the second surface, wherein the alignment members extend from the first surface at an angle that is different from angle $\alpha$ when viewed in a common plane;

a handle configured to mate with the boss, and operable to orient the augment guide block relative to the glenoid; and an augmenting device configured to be received within the slot, and operable to augment the glenoid at the angle $\alpha$, wherein the angle $\alpha$ corresponds to a surface of the glenoid implant.

12. The system according to claim 11, wherein the alignment members include a central alignment member and a peripheral alignment member.

13. The system according to claim 11, wherein the angle $\alpha$ is in the range of 10 degrees to 75 degrees.

14. The system according to claim 11, wherein the body is trapezoidal-shaped.

15. The system according to claim 11, wherein the augmenting device is a burr.

16. The system according to claim 11, wherein the guide slot is linear.

17. The system according to claim 11, wherein the guide slot includes an inlet and an outlet, and includes a radius of curvature between the inlet and the outlet.

* * * * *